(12) United States Patent
O'Donovan

(10) Patent No.: US 7,645,424 B2
(45) Date of Patent: Jan. 12, 2010

(54) REAGENT CUVETTE

(76) Inventor: Michael O'Donovan, Clonmar, Roxborough, Middleton, County Cork (IE)

( * ) Notice: Subject to any disclaimer, the term of this patent is extended or adjusted under 35 U.S.C. 154(b) by 0 days.

(21) Appl. No.: 11/434,211

(22) Filed: May 16, 2006

(65) Prior Publication Data

US 2006/0210450 A1    Sep. 21, 2006

Related U.S. Application Data

(63) Continuation of application No. PCT/IE2004/000162, filed on Nov. 18, 2004.

(60) Provisional application No. 60/523,104, filed on Nov. 19, 2003.

(51) Int. Cl.
*B01L 3/00* (2006.01)
*B01L 3/02* (2006.01)
*C12M 1/34* (2006.01)
*C12M 3/00* (2006.01)
*C12M 3/04* (2006.01)
*C12M 1/24* (2006.01)

(52) U.S. Cl. .................. 422/102; 422/99; 422/100; 435/288.1; 435/299.2; 435/304.1

(58) Field of Classification Search .............. 422/102, 422/99, 100; 435/288.1, 299.2, 304.1
See application file for complete search history.

(56) References Cited

U.S. PATENT DOCUMENTS

| 3,715,189 A | 2/1973 | Nighohossian ............... 23/259 |
| 5,954,268 A * | 9/1999 | Joshi et al. ..................... 239/34 |
| 6,495,373 B1 | 12/2002 | Mauchan ..................... 436/165 |
| 2002/0197631 A1 | 12/2002 | Lawrence et al. ............. 435/6 |

FOREIGN PATENT DOCUMENTS

| EP | 0 573 098 A2 * | 5/1993 |
| GB | 1026138 | 4/1966 |

* cited by examiner

*Primary Examiner*—Walter D Griffin
*Assistant Examiner*—Natasha Young
(74) *Attorney, Agent, or Firm*—Jacobson Holman PLLC

(57) ABSTRACT

A reagent cuvette has a first chamber with an inspection part and a socket, and a second chamber. The socket has four spikes at its base. Both chambers are sealed with a membrane. At the point-of-care the foil membrane of the first chamber is peeled away by the therapist (typically general practitioner doctor). A sample, such as blood, is added to the chamber using a pipette or other device to provide a verifiable quantity of sample. This provides a mixture of a buffer reagent supplied in the chamber and the sample injected into the inspection chamber at the point of care. The chamber is then inserted into the socket by gently pressing it down so that its foil membrane is broken by the spikes. This causes the starter reagent to drop down from within the second chamber into the inspection part of the first chamber. The inspection part is then inserted into an optical inspection instrument for analysis of the two reagents and the sample mixed together.

7 Claims, 4 Drawing Sheets

REAGENT CUVETTE

This is a continuation of PCT/IE04/000162 filed Nov. 18, 2004 and published in English, claiming benefit of U.S. provisional application No. 60/523,104, filed Nov. 19, 2003.

FIELD OF THE INVENTION

The invention relates to a reagent cuvette for sample analysis.

PRIOR ART DISCUSSION

At present, there is often a two-stage analysis of samples, namely point-of-care and laboratory analysis. Typically, the point-of-care analysis is performed using "dry chemistry" techniques. This is because such techniques are simple and convenient to perform: a sample being placed on a strip coated with a dry reagent and the strip being inserted into an inspection instrument.

The laboratory analysis is typically performed using "wet chemistry" techniques in which controlled volumes of fluid sample and reagent(s) are admixed and optically inspected. The "wet chemistry" techniques are regarded as being full and reliable tests, where the "dry chemistry" techniques are reliable only for screening purposes. Thus, a large number of patients may be unnecessarily subjected to the trouble and worry of further unwarranted tests beyond the point of care.

The invention addresses this problem.

SUMMARY OF THE INVENTION

According to the invention there is provided a reagent cuvette comprising at least first and second reagent chambers each containing a reagent, and a transfer means for transfer of a reagent to the first chamber from the second chamber for admixture of the reagents in the first chamber.

In one embodiment, the transfer means is for single and destructive use.

In one embodiment, the transfer means comprises a membrane across an opening of the second chamber, and a piercing member secured to the first chamber, whereby said second chamber membrane is pierced as the second chamber is pushed towards the first chamber In one embodiment, the first chamber comprises a socket for receiving the second chamber.

In one embodiment, the socket comprises the piercing member.

In one embodiment, the piercing member is located at the base of the socket.

In one embodiment, there are a plurality of piercing members mounted peripherally around the base of the socket.

In one embodiment, the second chamber is a friction fit in the first chamber.

In one embodiment, the socket and the second chamber have round cross-sectional configurations.

In another embodiment, the second chamber comprises a rim around an opening, the rim having a larger thickness than a wall of the second chamber, said rim being a friction fit within the socket.

In one embodiment, the first chamber comprises a lower inspection part having a wall which is transparent to analysis radiation, and the socket is located above the inspection part.

In one embodiment, the socket and the inspection part are integral.

In one embodiment, the socket is wider than the inspection part and they are interconnected by a shoulder, and said shoulder supports the piercing member.

In one embodiment, the first chamber comprises a manually removable cover.

In one embodiment, said cover is a peelable membrane.

In another aspect, the invention provides a method of performing wet chemistry sample analysis comprising the steps of:

providing a first chamber containing a controlled quantity of a first reagent,
providing a second chamber containing a controlled quantity of a second reagent,
adding a sample to the first chamber,
pressing the chambers together so that the reagent of the second chamber flows into the first chamber,
inspecting the contents of the first chamber.

In one embodiment, the action of pressing the chambers together causes a membrane across an opening of the second chamber to be pierced by a piercing member of the first chamber.

In one embodiment, the second chamber is pushed into a socket of the first chamber, said piercing member is within the socket, and the reagent of the second chamber flows downwardly into the first chamber when the membrane is pierced.

DETAILED DESCRIPTION OF THE INVENTION

Brief Description of the Drawings

The invention will be more clearly understood from the following description of some embodiments thereof, given by way of example only with reference to the accompanying drawings in which.

DESCRIPTION OF THE EMBODIMENTS

Figure 1:
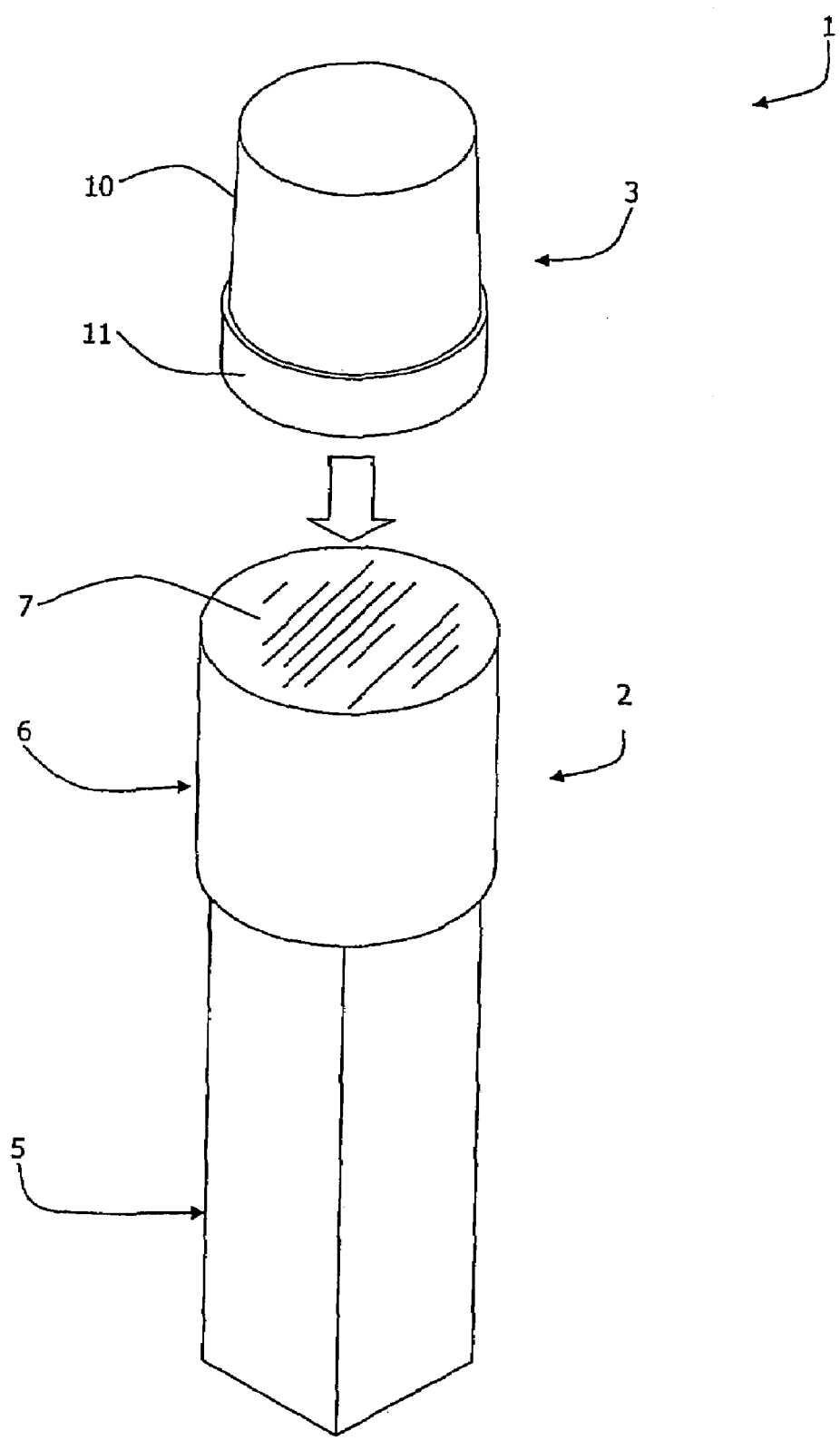
FIG. 1 is a perspective view of both parts of a reagent cuvette of the invention.
Figure 2:
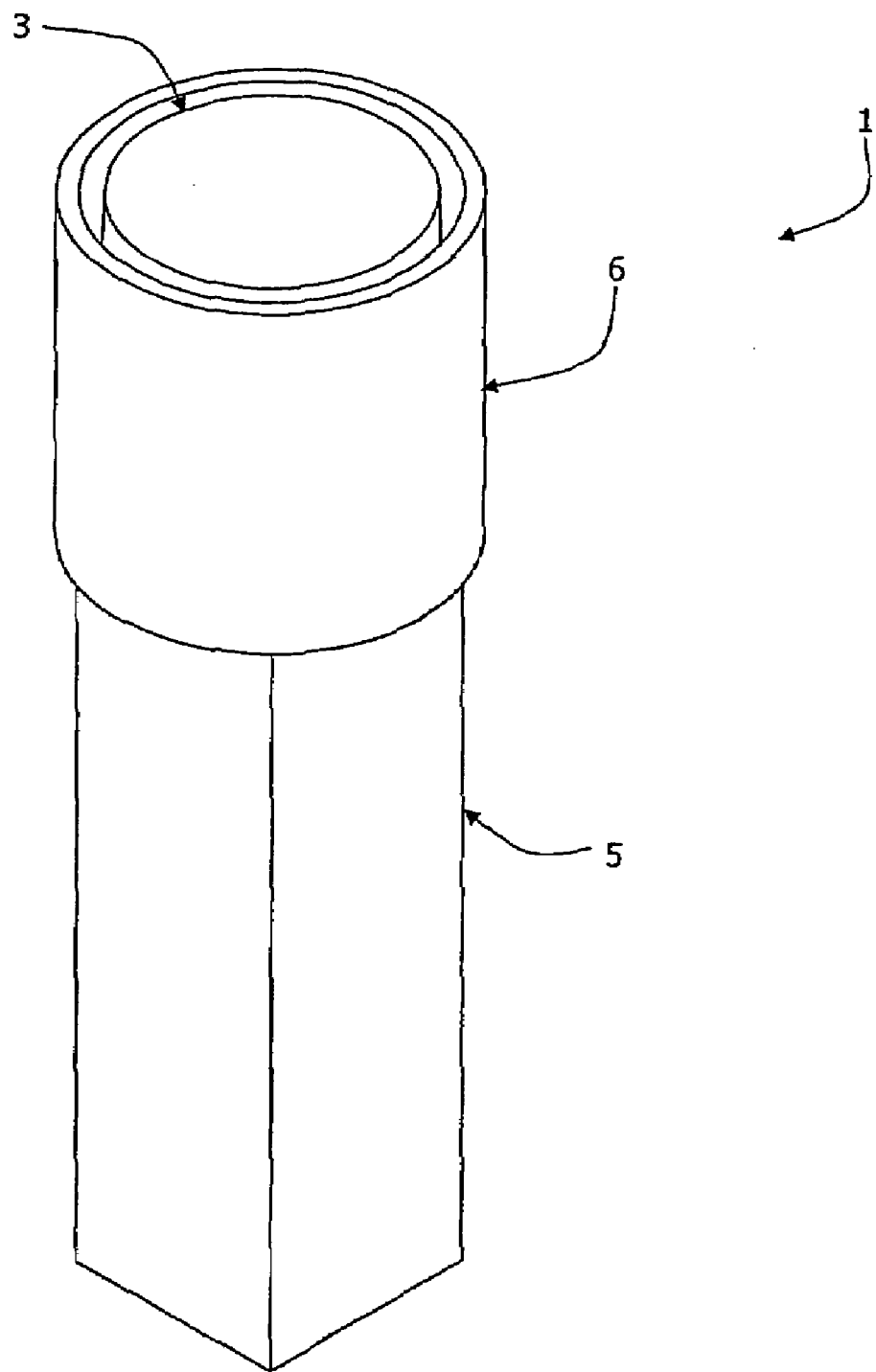
FIGS. 2, 3, and 4 are perspective, cut-away/sectional, and cross sectional views respectively of the cuvette with both parts together.

Referring to the drawings there is shown a reagent cuvette 1 for point-of-care analysis with laboratory accuracy. The cuvette 1 comprises two main parts, namely a first chamber 2 of approximately 64 mm height and a separate second chamber 3. The first chamber 2 and the second chamber 3 are of transparent plastics material. Both parts of the cuvette are of moulded plastics construction.

The first chamber 2 comprises an inspection part 5 and a socket 6 for receiving the chamber 3 in use, as described in more detail below. The inspection part 5 is of square cross-section, and extends for approximately two-thirds of the height of the chamber 2.

The socket 6 is of circular cross-section, tapering outwardly and upwardly at a small angle. It is wider than the inspection part 5, being connected to it by an integral shoulder. The chamber 2 is sealed by a foil membrane 7 extending across the top of the socket 6, and this seals in a buffer reagent supplied within the chamber 2.

The chamber 3 is of circular cross-section, having a wall 10 tapering outwardly towards its opening. The wall is thicker around its opening, forming a rim 11.

Figure 3:
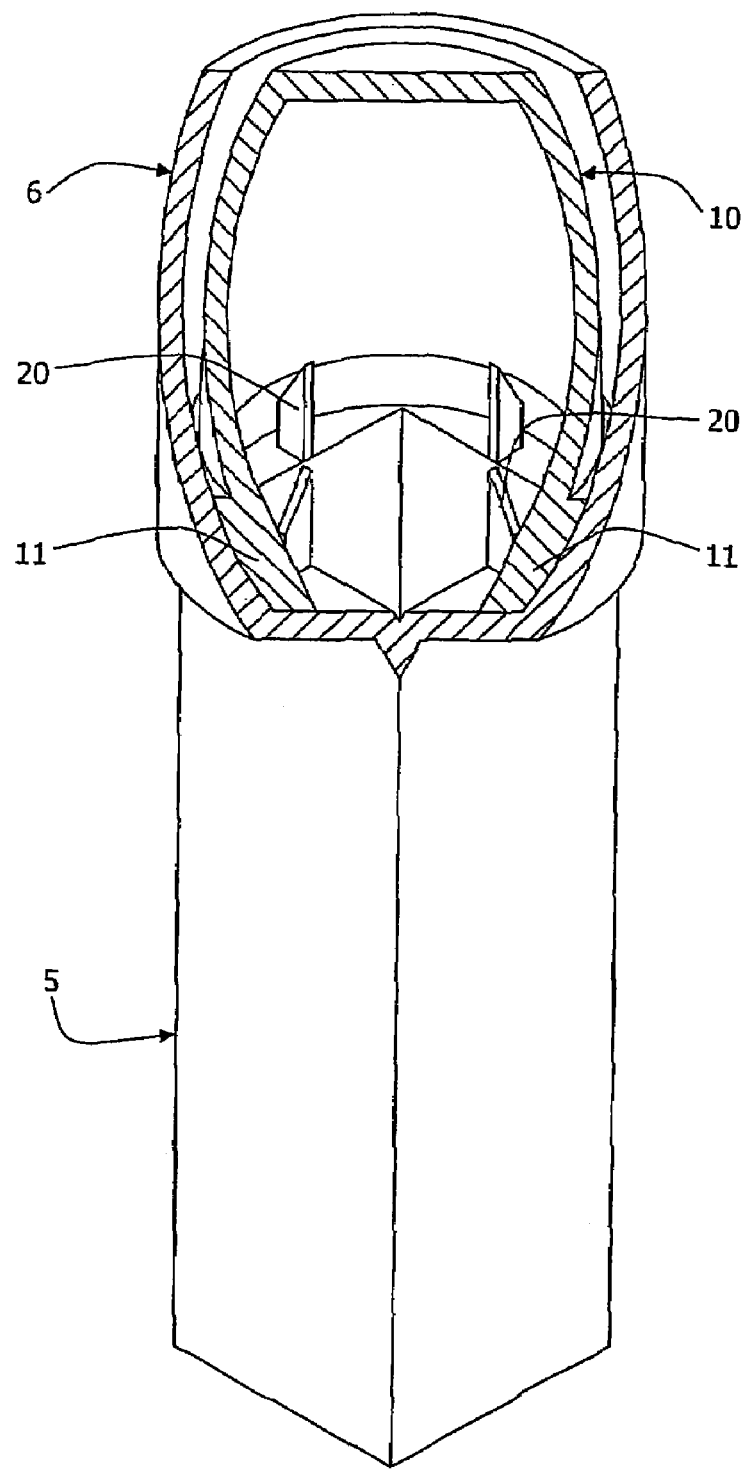
Figure 4:
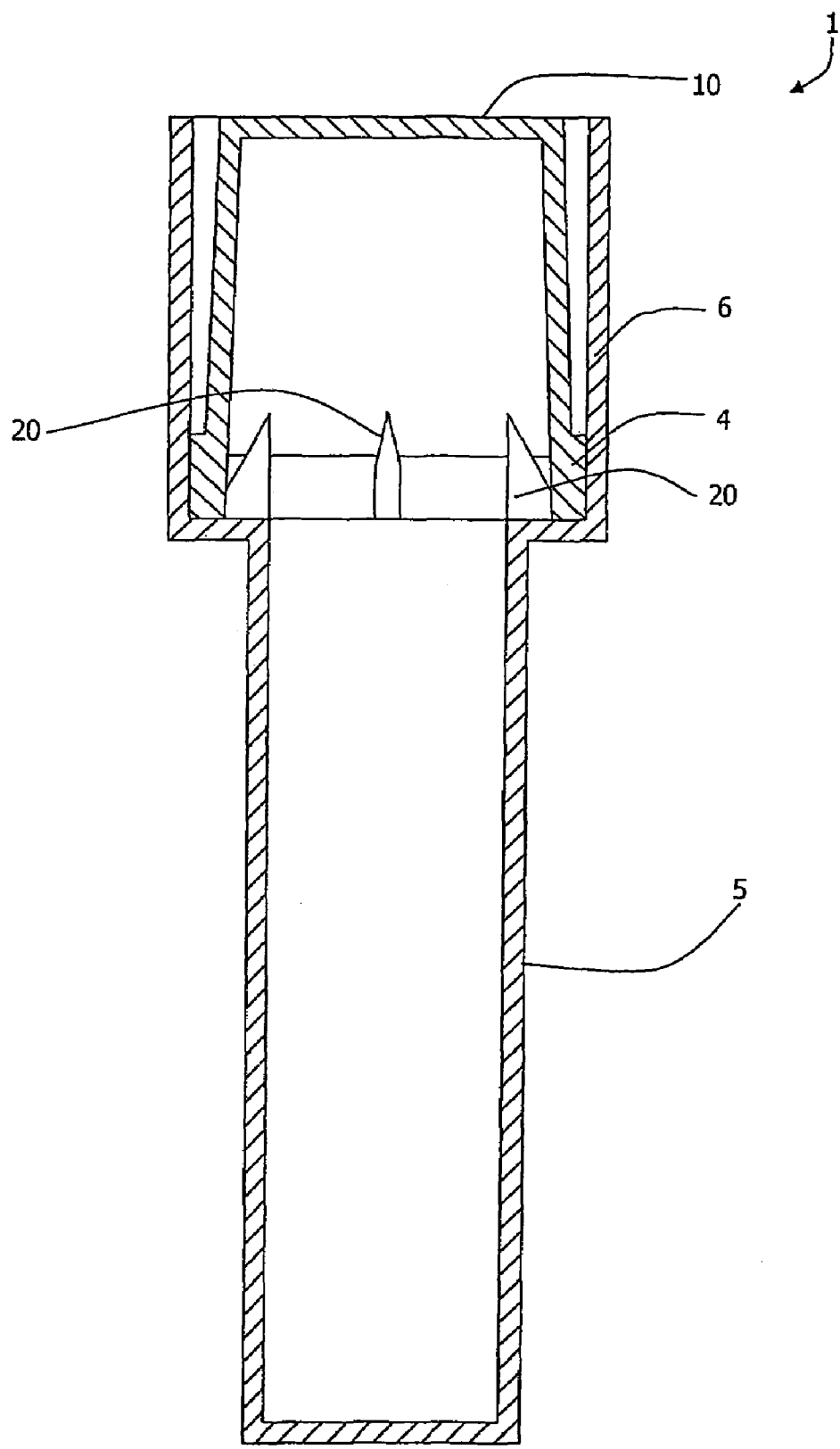

Referring particularly to FIGS. 3 and 4 there are four piercing members, in this embodiment spikes 20 equally spaced-apart around the base of the socket 6, on the shoulder connecting it to the inspection part 5. The spikes 20 are located so that there is just enough space for the rim 11 of the chamber 3 to fit between the spikes 20 and the wall of the socket 6 with a friction fit when the chamber 3 is pressed down into the socket 6 with its opening facing downwardly.

During manufacture, a buffer reagent is injected into the chamber 2, and the foil membrane 7 is sealed in place across the mouth of the socket 6.

Also, a starter reagent is injected into the chamber 3, and this is also sealed with a foil membrane (not shown).

Before completion of manufacture of the cuvette 1 the volumes of the reagents in the chambers 2 and 3 are verified and, of course, production records are generated for the chemical compositions and other relevant data concerning the reagents in both chambers.

In use, at the point-of-care the foil membrane 7 is peeled away by the therapist (typically general practitioner doctor). A sample, such as blood, is added to the chamber 2 using a pipette or other device to provide a verifiable quantity of sample. This provides a mixture of the buffer reagent supplied with the cuvette 1 and the sample injected into the inspection chamber 2 at the point of care.

The chamber 3 is then (while still sealed and with its opening facing down as shown in FIG. 1) inserted into the socket 6 by gently pressing it down so that its foil membrane is broken by the spikes 20. This causes the starter reagent to drop down from within the chamber 3 into the inspection part 5 of the chamber 2. The foil material of this membrane is both pierced and torn by the spikes 20 so that the full quantity of starter reagent drops into the inspection part 5.

The resultant transfer of the starter reagent into the mixture of sample and buffer reagent in the chamber 2 provides a mixture which can be analysed by an optical instrument at the point of care. The combination of the chambers 2 and 3 are effectively a single chamber, with the chamber 3 being a friction fit within the socket 6. The inspection part 5 is inserted into an optical inspection instrument for optical analysis of the sample/reagent mixture.

The quantities of both reagents are verifiable and accurate, so that when the inspection part 5 is inserted in an optical analysis instrument there is full and immediate analysis.

Thus, the point of care therapist can quickly and easily add the sample to the inspection chamber, and then quickly and easily add the starter reagent. Because of the repeatable, verifiable, and accurate nature of admixture of the sample and reagents the invention achieves laboratory-level inspection quality with point-of-care convenience and speed.

Thus, the invention provides for wet chemistry analysis at the point-of-care, effectively bringing fill laboratory analysis to the point-of-care in a simple and convenient manner.

The invention finds application at many locations such a point-of-care emergency clinics, non-laboratory facilities in hospitals, and remote doctor clinics in the developing world.

The invention is not limited to the embodiments described but may be varied in construction and detail. For example, there may be a different configuration of piercing member. In one example, a single spike is centrally located, being supported by radial support arms. In another embodiment, the piercing member takes the form of a blade to cut along a longer length of the membrane. The socket may alternatively include a cover for covering the starter reagent chamber after it has been inserted into the socket. This would ensure that it is held in place in the socket, and may also provide a tamper-evident seal for security purposes. Also, the socket may include a tamper-evident fastener for retaining the starter reagent chamber.

The invention claimed is:

1. A reagent cuvette comprising
   at least first and second reagent chambers each containing a reagent, and
   transfer means for transfer of a reagent to the first chamber from the second chamber for admixture of the reagents in the first chamber,
   the transfer means being for single and destructive use,
   the transfer means including a membrane across an opening of the second chamber sealing in the reagent of the second chamber, and piercing members secured to the first chamber, whereby said second chamber membrane is pierced as the second chamber is pushed towards the first chamber;
   the first chamber including a socket for receiving the second chamber, and the second chamber being in a friction fit in the socket;
   a plurality of the piercing members mounted peripherally around a base of the socket;
   the first chamber including a lower inspection part having a wall which is transparent to analysis radiation, and the socket being located above the inspection part; and
   the first chamber including a manually removable peelable membrane cover.

2. The reagent cuvette as claimed in claim 1, wherein the socket and the second chamber have round cross-sectional configurations.

3. The reagent cuvette as claimed in claim 1, wherein the second chamber includes a rim around an opening, the rim having a larger thickness than a wall of the second chamber, said rim being a friction fit within the socket.

4. The reagent cuvette as claimed in claim 1, wherein the socket and the inspection part are integral.

5. The reagent cuvette as claimed in claim 1, wherein the socket is wider than the inspection part, and the socket and the inspection part are interconnected by a shoulder, and said shoulder supports the piercing members.

6. A method of performing wet chemistry sample analysis with a reagent cuvette including at least first and second reagent chambers each containing a reagent, and a transfer means for transfer of a reagent to the first chamber from the second chamber for admixture of the reagents in the first chamber, the transfer means being for single and destructive use, the transfer means including a membrane across an opening of the second chamber sealing in the reagent of the second chamber, and piercing members secured to the first chamber, whereby said second chamber membrane is pierced as the second chamber is pushed towards the first chamber; the first chamber including a socket for receiving the second chamber, and the second chamber being in a friction fit in the socket when the second chamber is pressed down into the socket; a plurality of the piercing members mounted peripherally around a base of the socket; the first chamber including a lower inspection part having a wall which is transparent to analysis radiation, and the socket being located above the inspection part; the first chamber including a manually removable peelable membrane cover, the first chamber containing a controlled quantity of a first reagent and the second chamber contains a controlled quantity of a second reagent, the method comprising the steps of:
   peeling away the membrane cover from the first chamber, and adding a sample to the first chamber inspection part to provide a mixture of the first reagent and the sample,
   pressing the second chamber into the socket so that the piercing members of the first chamber pierce the membrane of the second chamber so that the reagent of the second chamber flows into the first chamber inspection part, and
   inspecting the contents of the first chamber.

7. A method as claimed in claim 6, wherein the inspection part of the first chamber is inserted into an optical inspection instrument for optical analysis of the sample/reagent mixture.

* * * * *

UNITED STATES PATENT AND TRADEMARK OFFICE
CERTIFICATE OF CORRECTION

PATENT NO. : 7,645,424 B2 Page 1 of 1
APPLICATION NO. : 11/434211
DATED : January 12, 2010
INVENTOR(S) : Michael O'Donovan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 39 days.

Signed and Sealed this

Sixteenth Day of November, 2010

David J. Kappos
*Director of the United States Patent and Trademark Office*